United States Patent
Duckett, III (10) Patent No.: US 10,598,918 B2
(45) Date of Patent: Mar. 24, 2020

(54) ENDOSCOPE LENS ARRANGEMENT FOR CHIEF RAY ANGLE CONTROL AT SENSOR

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 236 days.

(21) Appl. No.: 15/635,748

(22) Filed: Jun. 28, 2017

(65) Prior Publication Data
US 2019/0004305 A1    Jan. 3, 2019

(51) Int. Cl.
| | |
|---|---|
| G02B 23/24 | (2006.01) |
| G02B 3/00 | (2006.01) |
| G02B 23/04 | (2006.01) |
| H04N 5/225 | (2006.01) |
| A61B 1/00 | (2006.01) |
| A61B 1/05 | (2006.01) |

(52) U.S. Cl.
CPC ........ *G02B 23/243* (2013.01); *A61B 1/00096* (2013.01); *A61B 1/051* (2013.01); *G02B 3/0037* (2013.01); *G02B 23/04* (2013.01); *H04N 5/2251* (2013.01); *H04N 2005/2255* (2013.01)

(58) Field of Classification Search
None
See application file for complete search history.

(56) References Cited

U.S. PATENT DOCUMENTS

| | | | | |
|---|---|---|---|---|
| 5,704,896 A | * | 1/1998 | Fukunishi | A61B 1/05 348/340 |
| 5,954,633 A | * | 9/1999 | Hirata | G02B 23/2423 359/589 |
| 6,476,851 B1 | * | 11/2002 | Nakamura | A61B 1/00096 348/340 |
| 2002/0036832 A1 | * | 3/2002 | Schultz | G02B 13/143 359/649 |
| 2007/0030379 A1 | * | 2/2007 | Agranov | H04N 5/2254 348/340 |
| 2010/0036262 A1 | * | 2/2010 | Watanabe | A61B 1/043 600/478 |
| 2010/0059844 A1 | * | 3/2010 | Tanaka | G02B 3/0056 257/432 |
| 2014/0155694 A1 | * | 6/2014 | Murata | G02B 23/243 600/109 |
| 2016/0120397 A1 | * | 5/2016 | Namii | G02B 23/2415 348/68 |

\* cited by examiner

*Primary Examiner* — Kara E. Geisel
*Assistant Examiner* — Jarreas C Underwood
(74) *Attorney, Agent, or Firm* — Michael J. Loi; David N. Villalpando (57) ABSTRACT

Videoendoscope designs are provided including an objective and image sensor, preferably in the distal region, the image sensor having a micro-lens array with micro-lens offsets designed for a designated chief ray angle. The scope further includes a lens group having negative optical power optically arranged adjacent to the image sensor. The negative optical power serves to modify the chief ray angle characteristic of the lens group to more closely match that required by the image sensor and micro-lens array. Some designs include a non-linear distortion in the second lens group to compensate for non-linearly varying offsets in the sensor micro-lenses. Various lens group designs and sensor arrangements are provided.

22 Claims, 7 Drawing Sheets

ENDOSCOPE LENS ARRANGEMENT FOR CHIEF RAY ANGLE CONTROL AT SENSOR

BACKGROUND OF THE INVENTION

Field of the Invention

This invention relates to video endoscopes, and in particular to a scope using improved optical techniques to direct imaging light to sensor elements.

Description of the Background Art

The invention relates to optical instruments such as endoscopes, exoscopes, and borescopes having an image sensor assembly at the distal end of the instrument shaft. More particularly, the invention relates to image sensing systems that can produce a combined image from multiple image sensors located within the distal end of the instrument shaft, and to optical instruments incorporating such image sensing systems.

Instruments such as endoscopes and borescopes are used to allow a visual inspection of locations which are not readily accessible. For example, endoscopes are typically (although not exclusively) used in medical applications to provide a view of an area within a patient's body. Whether employed for medical or other applications, the instrument typically includes an elongated shaft of relatively small diameter extending from a handle to a distal end.

An imaging or viewing arrangement is included with the instrument to allow a user to obtain a view from the shaft distal end. This arrangement may include a system of lenses and a light conduit through the shaft to direct an image from the distal end to an eyepiece associated with the instrument handle. Alternatively, the imaging or viewing arrangement may include an electronic imaging device at the distal end of the instrument shaft. Such an electronic imaging device collects image data and communicates that data through the shaft and handle ultimately to a processing system that assembles the data to produce an image displayed on a suitable display device.

Image sensors with desirably high resolution are sometimes too large to fit into the distal tip of an endoscope. This problem often limits image resolution for endoscopes. With sensors available at the time of filing, an HD (1080p) sensor of adequate quality can fit inside a scope shaft of a 10 mm diameter. While videoendoscopes often require small sensors that can fit into the distal portion of an endoscope, unfortunately, it is rarely economical for state of the art sensor to be designed especially for endoscopic applications. More typically, the sensors employed for videoendoscopes are originally designed for the consumer electronics market (e.g., cell phones and laptops) or automotive applications. Such sensors often incorporate micro-lens arrays requiring the integrated optics to have a relatively steep chief ray angle. While this simplifies the design of compact, polymer optics such as those used in cell phones, it complicates the design of endoscopes.

There remains a need for ways to provide higher resolution capabilities for endoscopes using advanced miniaturized sensors, and to compensate for the chief ray angle often required by such sensors.

SUMMARY OF THE INVENTION

It is therefore an object of the invention to provide ways to compensate for the steep chief ray angle often required by image sensors. Lens assembly designs are provided that incorporate negative power near the focal plane to steepen the chief ray angle. Unlike other techniques for steepening the chief ray angle, this invention can be incorporated into systems where the sensor lies parallel to the endoscope shaft. Also included are techniques to address sensors requiring non-linear chief ray angles.

According to a first aspect of the invention, a videoendoscope includes an objective and image sensor, preferably in the distal region, the image sensor having a micro-lens array with micro-lens offsets designed for a designated chief ray angle. The scope further includes a lens group having negative optical power optically arranged adjacent to the image sensor. The negative optical power serves to modify the chief ray angle characteristic of the lens group to more closely match that required by the image sensor and micro-lens array. Some designs include a non-linear distortion in the second lens group to compensate for non-linearly varying offsets in the sensor micro-lenses.

According to a second aspect of the invention, an endoscopic instrument is provided which includes an instrument shaft having a distal end portion and a longitudinal axis spanning distal and proximal sides of the distal end portion. An image sensor is positioned to receive image light through the instrument shaft distal end portion. The image sensor includes a sensor array of active areas, and a micro-lens array including a plurality of micro-lenses arranged over the active areas such that the micro-lenses are progressively offset toward an optical center point of the sensor array as a distance from the respective active area to the optical center point increases, the progressive offset varying non-linearly with the distance. A lens assembly is provided including an objective lens or lens group positioned in the instrument shaft distal end portion to receive image light from an object space and pass the image light toward the proximal side, and a second lens group including one or more lenses and having negative optical power, the second lens group positioned between the objective lens or lens system and the image sensor, the negative optical power modifying a chief ray angle characteristic of the lens assembly to more closely align with the image sensor and micro-lens array non-linearly progressing offsets.

In a third aspect of the invention, an endoscopic instrument is provided including an instrument shaft having a distal end portion and a longitudinal axis spanning distal and proximal sides of the distal end portion. An image sensor is positioned in the instrument shaft distal end portion, the image sensor including a sensor array of active areas, and a micro-lens array including a plurality of micro-lenses arranged over the active areas such that the micro-lenses are progressively offset toward an optical center point of the sensor array as a distance from the respective active area to the optical center point increases, the progressive offset varying with the distance. A lens assembly includes an objective lens or lens group positioned in the instrument shaft distal end portion to receive image light from an object space and pass the image light toward the proximal side, and a second lens group including a plano-concave lens having negative optical power, the plano-concave lens positioned optically arranged adjacent to the image sensor, the negative optical power modifying a chief ray angle characteristic of the lens assembly to align with the image sensor and micro-lens array progressive offsets.

In some implementations of the third aspect, the image sensor includes a cover glass and the plano-concave lens is bonded to the cover glass.

In some implementations of the third aspect, the instrument includes a light-directing element between the objective lens group and the second lens group, constructed for re-directing light at approximately 90 degrees toward the second lens group.

In some implementations of the third aspect, the progressive offset of the micro-lenses varies non-linearly with the distance from the respective micro-lenses to the sensor array optical center point.

In a fourth aspect of the invention, an endoscopic instrument is provided including an instrument shaft having a distal end portion and a longitudinal axis spanning distal and proximal sides of the distal end portion. An image sensor is positioned in the instrument shaft distal end portion, the image sensor including a sensor array of active areas, and a micro-lens array including a plurality of micro-lenses arranged over the active areas such that the micro-lenses are progressively offset toward an optical center point of the sensor array as a distance from the respective active area to the optical center point increases, the progressive offset varying with the distance. A lens assembly includes an objective lens or lens group positioned in the instrument shaft distal end portion to receive image light from an object space and pass the image light toward the proximal side, and a second lens group including a bi-concave lens having negative optical power, the bi-concave lens positioned optically arranged adjacent to the image sensor, the negative optical power modifying a chief ray angle characteristic of the lens assembly to align with the image sensor and micro-lens array progressive offsets.

In some implementations of the fourth aspect, the image sensor includes a cover glass and the bi-concave lens is bonded to the cover glass.

In some implementations of the fourth aspect, the progressive offset of the micro-lenses varies non-linearly with the distance from the respective micro-lenses to the sensor array optical center point.

In some implementations of the various aspects and implementations thereof, the negative optical power may modify the chief ray angle characteristic of the lens assembly enough to successfully integrate the image sensor and micro-lens array non-linearly progressing offsets. In some implementations, the negative optical power modifies the chief ray angle characteristic of the lens assembly to match the lens assembly to a steep chief ray angle characteristic of the image sensor of at least 20 degrees.

In some implementations of the various aspects and implementations thereof, the negative optical power modifies the chief ray angle characteristic of the lens assembly to match that required by the image sensor and micro-lens array non-linearly progressing offsets.

In some implementations of the various aspects and implementations thereof, the objective lens or lens group, the second lens group, and the image sensor are positioned in the instrument shaft distal end portion.

In some implementations of the various aspects and implementations thereof, the second lens group exhibits a non-linear distortion across at least some of a working area of the second lens group.

In some implementations of the first or second aspects, the second lens group includes a plano-concave lens having a planar side facing toward the image sensor, and a plano-convex lens between the plano-concave lens and the image sensor, having a planar side facing the image sensor. The second lens group may exhibits a non-linear distortion across at least some of a working area of the second lens group.

In some implementations of the various aspects and implementations thereof, the instrument includes a reflecting optical surface between the second lens group and the objective. The reflecting optical surface includes a prism. The reflective optical surface may include a beam splitter. The reflecting optical surface and at least some portion of the second lens group having negative optical power may be integrated into a single optical element.

In some implementations of the first or second aspects, the second lens group includes a plano-convex lens.

In some implementations of the first or second aspects, the second lens group includes a surface with negative optical power and a surface with positive optical power.

In some implementations of the first or second aspects, the second lens group includes an element with negative optical power and an element with positive optical power. The objective lens or lens group may exhibit a non-linear chief ray angle characteristic.

In some implementations of the various aspects and implementations thereof, some part of the second lens group with negative optical power is in contact with the image sensor, and may be cemented to the image sensor.

Further scope of the applicability of the present invention will become apparent from the detailed description given hereinafter. However, it should be understood that the detailed description and specific examples, while indicating preferred embodiments of the invention, are given by way of illustration only, since various changes, combinations and modifications within the scope of the invention, as defined in the claims, will become apparent to those skilled in the art from this detailed description.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF THE DRAWINGS

As used herein, elements (e. g., sensors and lenses) that are "optically arranged" in relation to other elements, refers to the elements' position along an optical path shared by first and other elements. For example, a relay lens group optically arranged between an image sensor and an objective, means that the relay lens group occupies a portion of the optical path that light travels (i.e., from the objective to the image sensor) for capturing images or video. "Optical image" is an image formed by the light rays from a self-luminous or an illuminated object that traverse an optical system or element. As used herein, the term "chief ray angle characteristic" refers to the effect of an optical element on the chief ray angle on the image side, not the object side, as measured in the standard way, with central rays perpendicular to the sensor being the zero reference angle.

Figure 1:
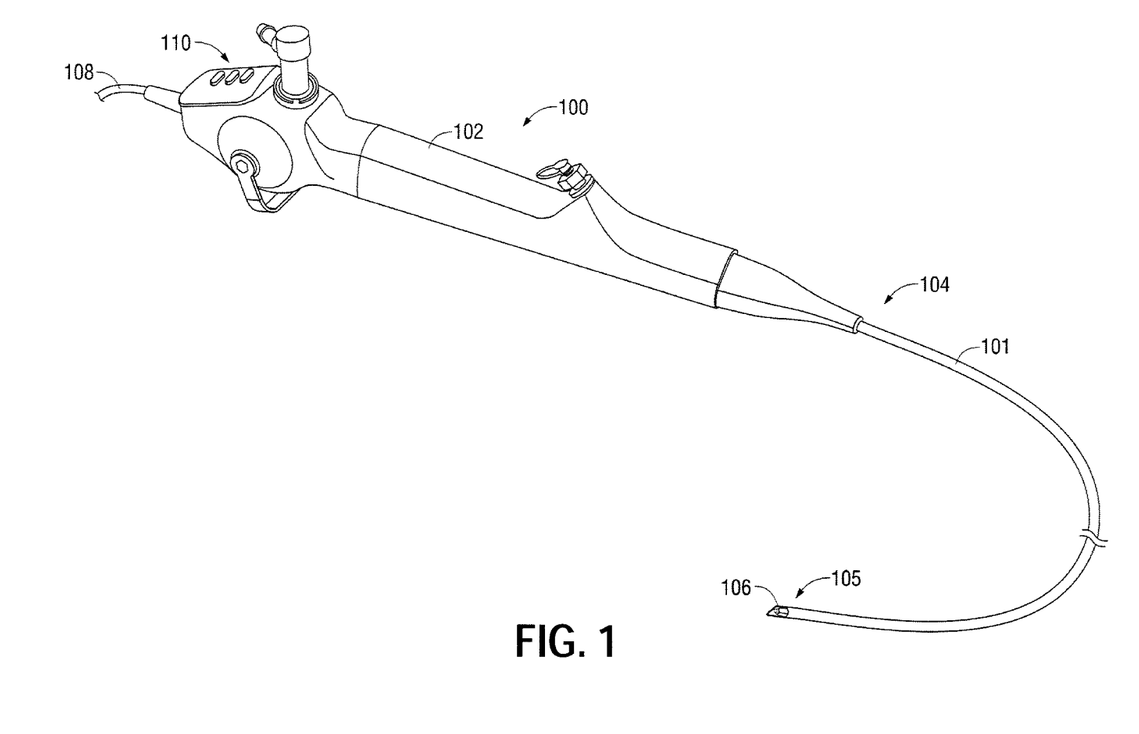
FIG. 1 is a perspective view of an endoscope instrument according to an example embodiment.

Referring to FIG. 1, depicted is a perspective view of an optical instrument 100 employing an improved optical assembly according to one aspect of the present invention includes an elongated shaft 101 and a handle 102. Shaft 101 extends from a proximal end shown generally at reference numeral 104 connected to handle 102 to a distal end generally indicated at reference numeral 105. A distal end portion 106 is included at the shaft distal end 105. The image sensors according to the present invention are located in distal end portion 106, although it is not shown in FIG. 1 due to the scale of the figure. The shown shaft 101 is a flexible implementation, but rigid-shaft implementations are also possible.

Instrument 100 receives electrical operating power through a cable 108 which extends from a proximal end of handle 102 in this example instrument. This power may be used to operate one or more light sources and other electronic elements mounted within distal end portion 106, including multiple electronic image sensors. Also, data signals from such an imaging device may be communicated through appropriate conduits within shaft 101 and handle 102 to cable 108. These data signals may be communicated through cable 108 to processing equipment (not shown) which processes the image data and drives one or more video monitors to display the images collected at distal end 105 of instrument 100. Those familiar with endoscopes and borescopes will appreciate that instrument 100 includes a number of additional features such as controls 110 for controlling the operation of the instrument. Although data transmission relating to the image sensors will be described further below, the general operation and control of instrument 100 will not be described further herein in order to avoid obscuring the present invention in unnecessary detail. Preferably the designs and techniques herein are employed as improvements to a videoendoscope with a distal mounted image sensor arrangement), however this is not limiting and the same techniques may be applied to endoscopes using a camera head arrangement in which the image sensor is positioned at or outside the proximal end of the endoscope shaft.

Figure 2:
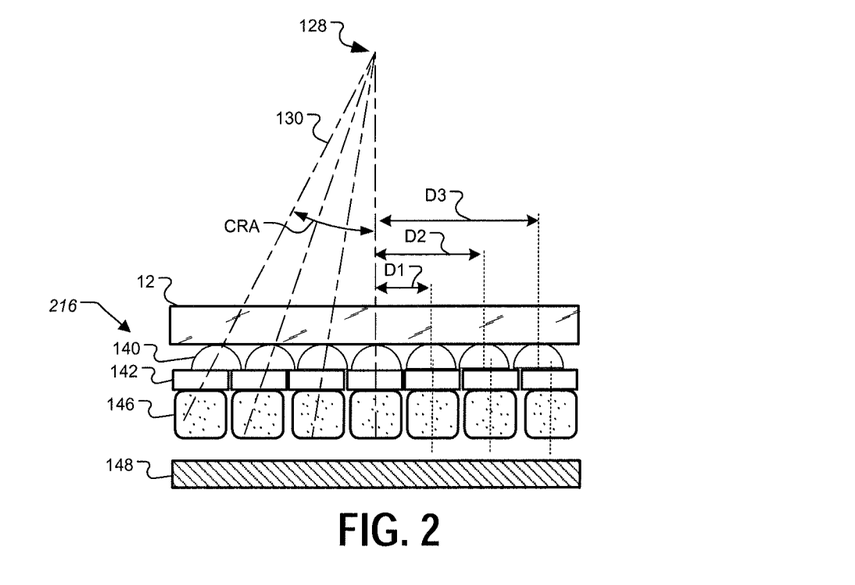
FIG. 2 shows a cross sectional diagram of a sensor which may be employed in some embodiments.

FIG. 2 shows a cross sectional diagram of a sensor which may be employed in some embodiments. The diagram is helpful for illustrating the structure of commercial image sensors which are often designed for smartphones and tablets, but often represent the best available mass produced miniaturized image sensors. The diagram generally shows an idealized cross section of an image sensor 216, depicting light rays 130 impinging on the sensor 216 from a central point 128 on the system optical axis. The depicted sensor is idealized to show a small array with very few pixel elements in order to illustrate offsets and angles involved, where typically an image sensor will have an array of many hundreds of pixels in each dimension, for example 1080 pixels along one dimension, with each pixel often having multiple photodiodes 146 to sense different colors for the pixel. The sensor construction will vary with different technologies and may include more or less layers, with this example shown for illustration purposes. Sensor 216 includes a cover glass 12, which is typically fixed in packaging (not shown) or an integrated sensor assembly. Beneath cover glass 12 are micro-lenses 140 which collect and direct the impinging light toward the photodiodes 146. Typically each photodiode 146 is covered by a color filter 142 to allow the desired color to pass. The chief ray angle CRA is depicted as the angle between directly perpendicular light shown at the center photodiode, and the angle at which the edge pixels are designed to receive light. A metalized interconnect layer (not shown) may be between the color filter 142 layer and the photodiode 146 layer, or between the photodiode 146 layer and the carrier substrate 148, and in some cases may be integrated with the photodiode layer. Some sensor designs place the micro-lens 140 layer on-chip, that is, under the color filter 142 layer. To improve the light collection to each photodiode 146, some of the micro-lenses 140 have an offset from the center of the photodiode, as depicted by the distances D1, D2, and D3 which mark the distance from the array center to each micro-lens 140 center. The micro-lenses 140, typically each associated with a single photodiode, are progressively offset toward an optical center point of the sensor array as a distance from the respective photodiode to the optical center point increases. As can be seen versus the vertical lines at the center of photodiodes 146, the micro-lens offset increases toward the edge of the array, allowing light to be collected at an increasing angle toward the array center. The offset may increase linearly with the distance from the center, or in some sensors may be designed to increase non-linearly. This effect is to allow the use of compact typically low price polymer optics in the design of smartphones and tablets. Such sensors are often designed with a steep CRA of approximately 20 degrees or more. However this presents difficulties in using such sensors with less compact optical assemblies which are typically designed to provide less steep chief ray angles, with a more perpendicular impingement of light across the entire sensor array, having less angular variation across the array.

Figure 3:
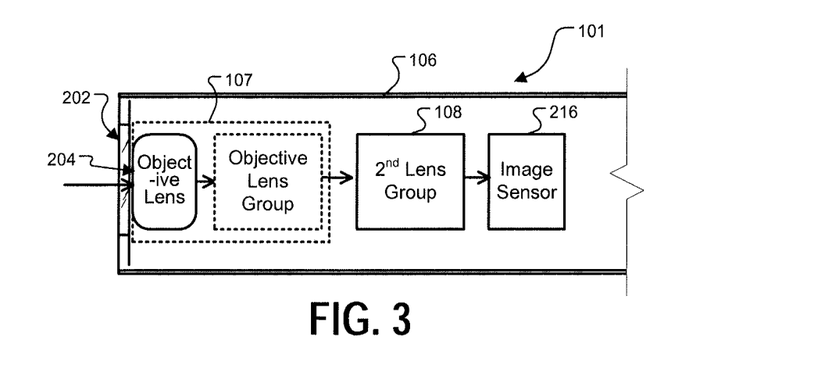
FIG. 3 is a cross sectional diagram of a portion of an endoscopic instrument according to an example embodiment of the invention.

FIG. 3 is a cross sectional diagram of a portion of an endoscopic instrument according to an example embodiment of the invention. A distal end portion 106 of the instrument shaft 101 is shown in a mixed cross section and block diagram form. Other elements such as light emitting devices may also be mounted at the distal end portion but are not shown so as not to obscure the important parts of the invention. As the depicted arrows show, image light enters the scope end through cover glass 202 and passes through an objective lens 204, which may or may not be part of a larger objective lens group 107. The objective lens or lens group is positioned in the instrument shaft distal end portion to receive image light from an object space outside the scope and pass the image light in the proximal direction. Typically elements 107 and 108 make up a lens assembly constructed together to form a mechanically stable optical path, but in some embodiments there may be separation between the elements of such a lens assembly. Optically arranged in the proximal direction from the objective lens or lens group is a second lens group including one or more lenses and having negative optical power, versions of which will be further described below. The second lens group is optically positioned between the objective lens or lens system and the image sensor 216. The image sensor 216 is positioned to receive image light through the instrument shaft distal end portion, and includes a sensor array of active areas and a micro-lens array including a plurality of micro-lenses arranged over the active areas such that the micro-lenses are progressively offset toward an optical center point of the sensor array as a distance from the respective active area to the optical center point increases, as described above with respect to FIG. 2. The progressive offset in some versions varies non-linearly with the distance, and in other versions does not. Preferably, the element(s) of the second lens group 108 having negative optical power are placed at or near the image plane of the optical path, that is, optically adjacent to the image sensor, and more preferably physically adjacent to the image sensor, such as mounted to the image sensor cover glass. For versions in which the image sensor(s) is located in the distal tip, the image sensor(s) is typically positioned between 3 mm and 15 mm away from the objective lens. However, the commercial image sensors employed are often designed to be used with different objectives and optical channel designs, and so may require light to be received at a steep chief ray angle for optimal operation. While the embodiments described herein include the image sensor assembly and the second lens group in the distal tip of the instrument shaft, this is not limiting and similar benefits of compatibility with commercially mass produced sensors may be had with endoscopic instrument designs in which the image sensor is located elsewhere, such as in a proximal portion of the scope shaft, or more commonly in a camera head to which the scope shaft is attached. The various embodiments of a second lens group described herein, and variations thereof, may be employed with an image sensor assembly located in a camera head portion of an endoscopic instrument.

Second lens group 108 is constructed such that the one or more lenses with negative optical power modify a chief ray angle characteristic of the lens assembly to more closely align with the image sensor and micro-lens array offsets. Such design may be used to match the lens assembly to an image sensor 216 having a steep chief ray angle characteristic of 20 degrees or more. In some embodiments, the negative optical power modifies the chief ray angle characteristic of the lens assembly to match that required by the image sensor and micro-lens array progressing offsets. In some embodiments, the negative optical power modifies the chief ray angle characteristic of the lens assembly enough to successfully integrate the image sensor and micro-lens array progressing offsets. While the lens assembly and image sensor are shown optically arranged in a linear sequence, this is not limiting and some versions may orient the sensor at a right angle or other angle from the longitudinal axis of the scope shaft distal end. The designs herein are also suitable for use with flexible or rigid scope shafts where the distal end portion itself is rigid.

Figure 4:
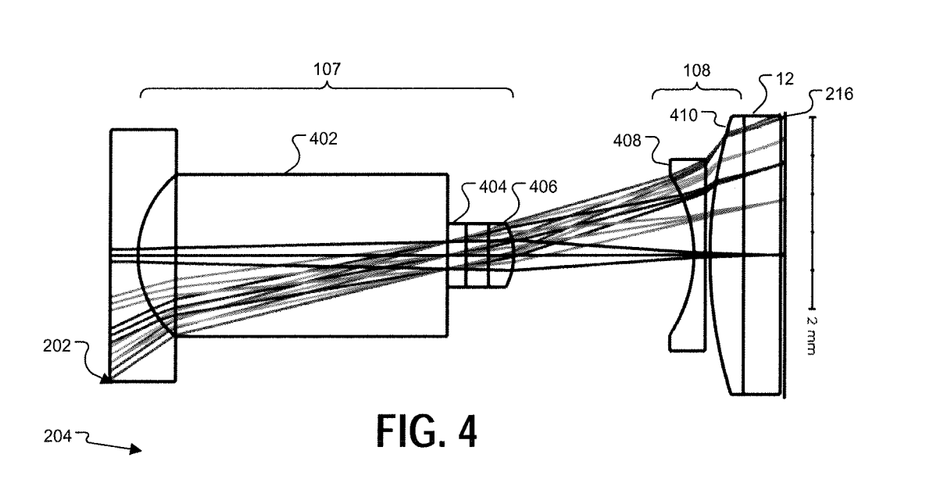
FIG. 4 is a cross section diagram of a lens assembly for use with a videoendoscopes instrument according to another example embodiment of the invention.

FIG. 4 is a cross section diagram of a lens assembly for use with a videoendoscopes instrument according to another example embodiment of the invention. Only the lenses and sensor are shown, with a partial ray diagram included illustrating the effect of the optical elements. Objective lens 204 in this version is cemented to a concave depression in the cover glass 202. Optically arranged or attached at the proximal side of objective lens 204 is a spacing element 402 such as a rod lens or square prism. Optically arranged at the proximal side of spacing element 402 is a flat optical element 404 that includes an aperture stop printed at its distal side. Next, optically arranged to the proximal is a doublet 406, preferably an achromatic doublet, with a positive optical power including a plano-concave lens bonded to a bi-convex lens. The concave-convex union of doublet 406 is a very slight concave that may appear straight in the drawing. Elements 404 and 406 are preferably smaller than spacing element 402 and bonded to its proximal side. In place of the doublet a plano-plano element may be bonded to a plano-convex element, with the flat element serving as an IR cut filter. The objective lens group 107 in this version includes elements 204, 402, 404, and 406.

Next the light passes across a gap to the second lens group 108, which has negative optical power as described to modify a chief ray angle characteristic of the lens assembly to more closely align with the image sensor and micro-lens array offsets. In this embodiment, second lens group 108 may provide a non-linear modification of chief ray angle characteristic in order to match or more closely match a non-linear variation from the optical center of image sensor 216, as discussed above. This is achieved with plano-concave lens 408 and plano-convex lens 410, which is preferably bonded to the image sensor cover glass 12. Concave-plano lens 408 is mounted as shown optically arranged in front of plano-convex lens 410, with the planar side facing proximally such that lens 408 has a negative optical power. Plano-concave lens 408 is preferably of a smaller diameter than plano-convex lens 410. Lens 410 has a positive optical power and directs the image light to image sensor 216 with the desired chief ray angle to more closely align with the chief ray angle for which image sensor 216 is designed. The differing radial sizes in the concave and convex portions of lenses 408 and 410, along with their arrangement, can provide a non-linear optical distortion in the radial direction from the center of the image light. As such, second lens group 108 is constructed such that lens 408 with negative optical power modifies a chief ray angle characteristic of the lens assembly to more closely align with the image sensor and micro-lens array offsets. Such design may be used to match the lens assembly to an image sensor 216 having a steep chief ray angle characteristic of 20 degrees or more. In some embodiments, the negative optical power modifies the chief ray angle characteristic of the lens assembly to match that required by the image sensor and micro-lens array progressing offsets. In some embodiments, the negative optical power modifies the chief ray angle characteristic of the lens assembly enough to successfully integrate the image sensor and micro-lens array progressing offsets. While the lens assembly and image sensor are shown optically arranged in a longitudinal sequence, this is not limiting and some versions may orient the sensor at a right angle or other angle from the longitudinal axis of the scope shaft distal end. The designs herein are also suitable for use with flexible or rigid scope shafts.

A 2 mm scale is shown on FIG. 4 for example purposes to illustrate various types of sensors which may be employed with the techniques herein. For example, sensor 216 may be a small size such as a 2728×1549 μm image sensor with a full HD (1920×1080) sensor pixel array. This is not limiting many other suitable sensors of other sizes may be employed with the techniques herein, especially as sensor technology improves. For example, a 2945×2214 μm image sensor (5 MP array) or a 5320×3960 μm image sensor (13 MP array). The scale of FIG. 5 shows use with an even smaller sensor array.

Figure 5:
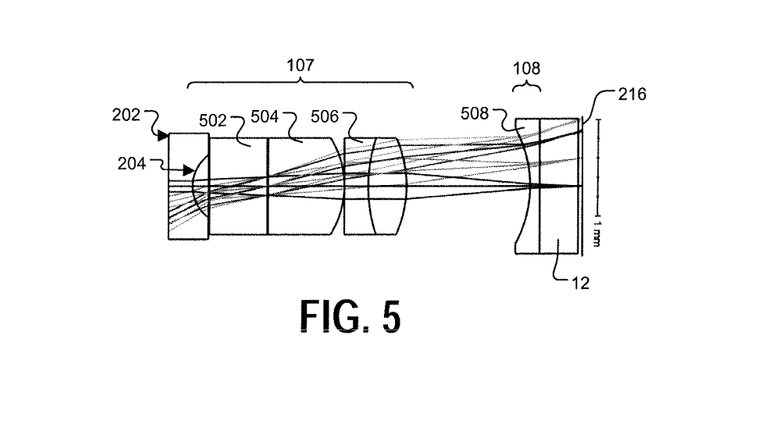
FIG. 5 shows a cross section diagram of a lens assembly designed with a smaller image sensor array for use in a videoendoscopes device according to another embodiment of the invention.

FIG. 5 shows a cross section diagram of a lens assembly designed with a smaller image sensor array for use in a videoendoscopes device according to another embodiment of the invention. This cross section diagram again shows only the lenses and sensor element with light rays bundles drawn to illustrate the optical path. In this version the objective lens group 107 includes objective lens 204 and elements 502, 504, and 506. Objective lens 204 is optically arranged next to a spacing element 502, which has an aperture printed at its proximal side. Optically arranged next is a plano-concave lens 504 having a positive optical power. Next is a doublet lens 506, preferably an achromatic doublet, of a plano-concave lens and a bi-convex lens, which also has a positive optical power and directs the focused light across a gap toward second lens group 108. The second lens group includes a single plano-concave lens 508 arranged with the planar side adjacent to the sensor cover glass 12, preferably attached with cement. Lens 508 has a negative optical power and modifies a chief ray angle characteristic of the lens assembly to more closely align with the image sensor and micro-lens array offsets. Again, such design may be used to match the lens assembly to an image sensor 216 having a steep chief ray angle characteristic of 20 degrees or more. As with other embodiments herein, in some cases the negative optical power modifies the chief ray angle characteristic of the lens assembly to match that required by the image sensor and micro-lens array progressing offsets. In some embodiments, the negative optical power modifies the chief ray angle characteristic of the lens assembly enough to successfully integrate the image sensor and micro-lens array progressing offsets.

FIGS. 6-10 are cross section diagrams showing several variations of different lens assemblies for use with a videoendoscopes according to embodiments in which an image sensor oriented parallel to the endoscope shaft, rather than perpendicular, with the image sensor array facing in the perpendicular direction to the shaft longitudinal axis. Such a configuration may be useful for videoendoscopes designs in which the image sensor, including its packaging or housing assembly, is too large to fit in the cross sectional area of the endoscope shaft that is employed. In FIGS. 6-10, the objective lens group 107 is structured similarly to that of FIG. 5, directing image light to doublet lens 506, and different variations are shown for the structure of second lens group 108. However, this is not limiting and many suitable variations are possible for the objective lens group 107. From the objective lens group 108, the light passes to a light directing element, which in this example is a right angle prism 602, which reflects the light at a right angle downward toward sensor 216.

Figure 6:
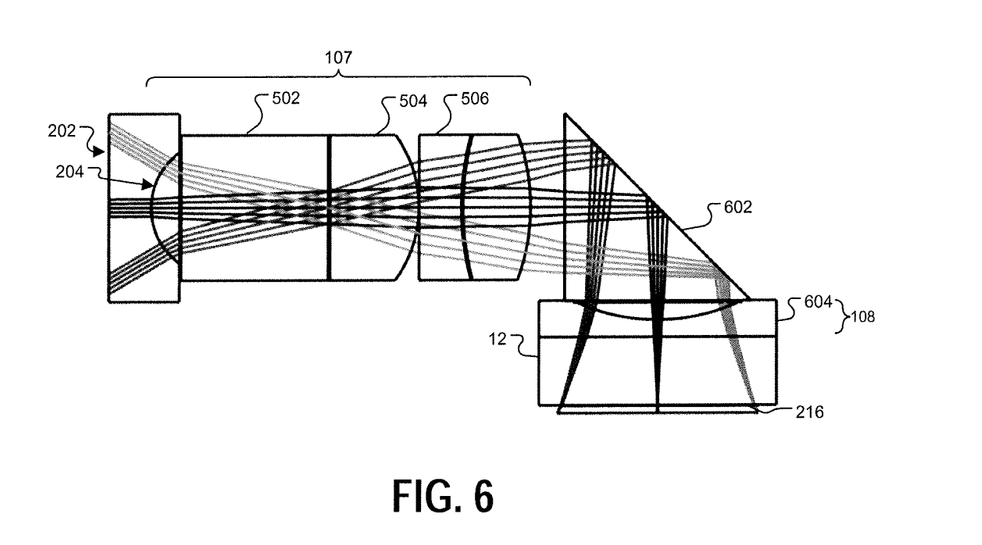
FIGS. 6-9 are cross section diagrams showing several variations of different lens assemblies for use with a videoendoscopes according to embodiments in which an image sensor oriented parallel to the endoscope shaft, rather than perpendicular, with the image sensor array facing in the perpendicular direction.
Figure 7:
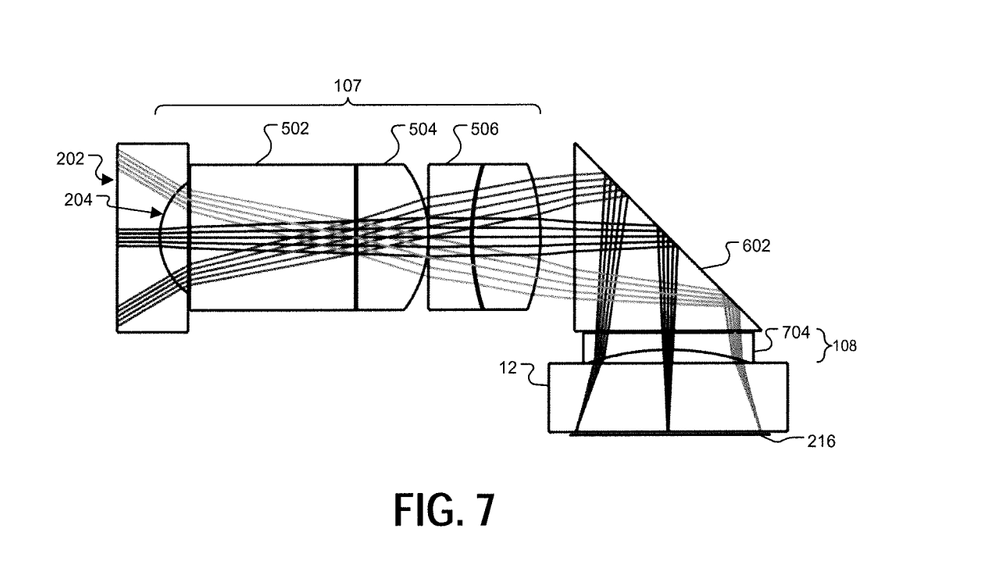
Figure 8:
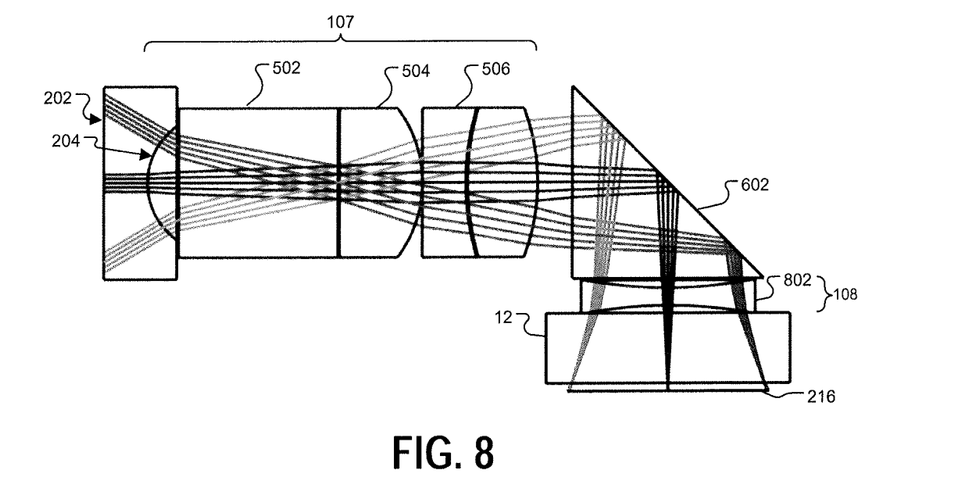

In the version of FIG. 6, receiving the light from the light directing element is a plano-concave lens 604, which in this version constitutes the second lens group 108. Lens 604 is optically arranged between the light directing element and the image sensor cover glass 12, and may be bonded to either or both of them. As depicted by the divergence of light rays, plano-concave lens has a negative optical power. Lens 604 is optically arranged next to cover glass 12 of image sensor 216, and preferably bonded to the cover glass 12. Lens 604 has a negative optical power and modifies a chief ray angle characteristic of the lens assembly to more closely align with the image sensor and micro-lens array offsets. In the version of FIG. 7, the second lens group includes a plano-concave lens 704, which oriented with the concave side facing down, or toward cover glass 12, versus the orientation in the version of FIG. 6 with concave side facing upwards or away from cover glass 12. In both cases, the lenses 604 and 704 have a negative optical power. Lens 704 may also be bonded to elements 602 or 12. The version of FIG. 8 includes a bi-concave lens 802, having a negative optical power, in the same location.

Figure 9:
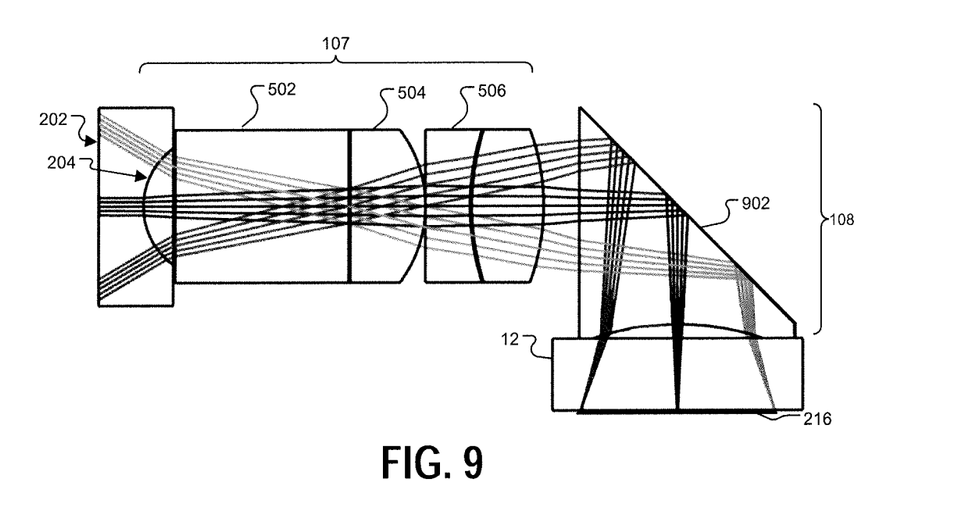

In the version of FIG. 9, the light directing element, in this case a right angle prism 902, is structured to include a concave lens surface on the side facing image sensor 216. Right angle prism 902 therefore functions optically as the prism and as a concave lens with a negative optical power optically arranged between the prism and the image sensor. This allows a single optical element to provide both functions and simplifies construction. It may also require less total space in the dimension shown as vertical on the drawings, allowing a larger image sensor assembly to fit into a small diameter shaft than the other designs might allow.

Figure 10:
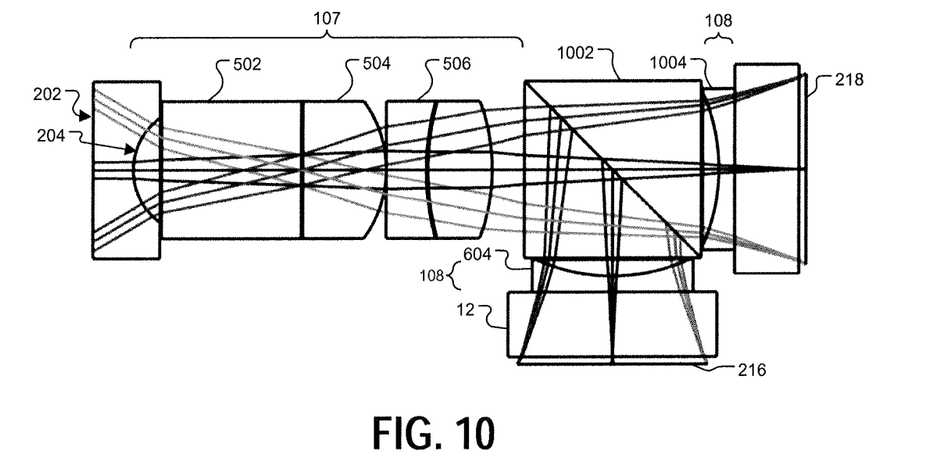
FIG. 10 is a cross section diagram of yet another example, in which a beam splitter prism is used as a light directing element.

FIG. 10 is a cross section diagram of yet another example embodiment, in which a beam splitter prism is used as a light directing element. As depicted, in this version, a beam splitter prism cube 1002 is optically arranged between the objective lens group 107 and the second lens group 108 to receive the image light from the objective lens group. The prism cube 1002 may be constructed with suitable prisms to split the incoming light toward two sensors 216 and 218, each positioned to receive a portion of the image light. For example, the prism 1002 may be constructed with two right angle prism joined together, with a dielectric, achromatic beamsplitter coating along the interface between the prisms. As can be seen in the light ray diagram, the light is split with a first portion of the light reflected downward while the other portion is passed straight through the prism 1002. Prism cube 1002 may also be another type of light splitter such as a dichroic prism or a trichroic prism, for example. Optically arranged between prism 1002 and image sensor 216 is a plano-concave lens 604 having negative optical power. Similarly, optically arranged between image sensor 218 and beam splitter prism 1002 is a second plano-concave lens 1004 having a negative optical power. The lenses may be bonded to their respective sensor cover glass.

The arrangement of FIG. 10 may be useful for many different scenarios in which multiple different imaging characteristics are desired. For example, it may allow the two image sensors to capture separate spectral ranges of image light, to have different exposures, or to have separate focal planes for providing an extended field of depth. The depicted arrangement may also be used to split the image field between two image sensors, thereby creating a higher resolution image than would be achievable with a single sensor fitting in the same cross-sectional area of an endoscope shaft. Such a split-image sensor arrangement is found in U.S. patent application Ser. No. 15/400,137, filed 6 Jan. 2017, and titled "Endoscope Incorporating Multiple Image Sensors for Increased Resolution," which application is hereby incorporated by reference for all purposes.

As with the other embodiments herein, the designs of FIGS. 6-10 may be used to match the lens assembly to an image sensor 216 (or 218, FIG. 10) having a steep chief ray angle characteristic of 20 degrees or more. In some cases the negative optical power modifies the chief ray angle characteristic of the lens assembly to match that required by the image sensor and micro-lens array progressing offsets. In some embodiments, the negative optical power modifies the chief ray angle characteristic of the lens assembly enough to successfully integrate the image sensor and micro-lens array progressing offsets. The concave face(s) of the lenses may also be created with an irregular concavity to create a non-linear distortion and thereby more closely match a non-linearly progressing offset as is used in some commercial sensors. Further, for the various embodiments herein, while specific lenses are described, other suitable lens and lens group designs may be employed to achieve the negative optical power required.

Figure 11:
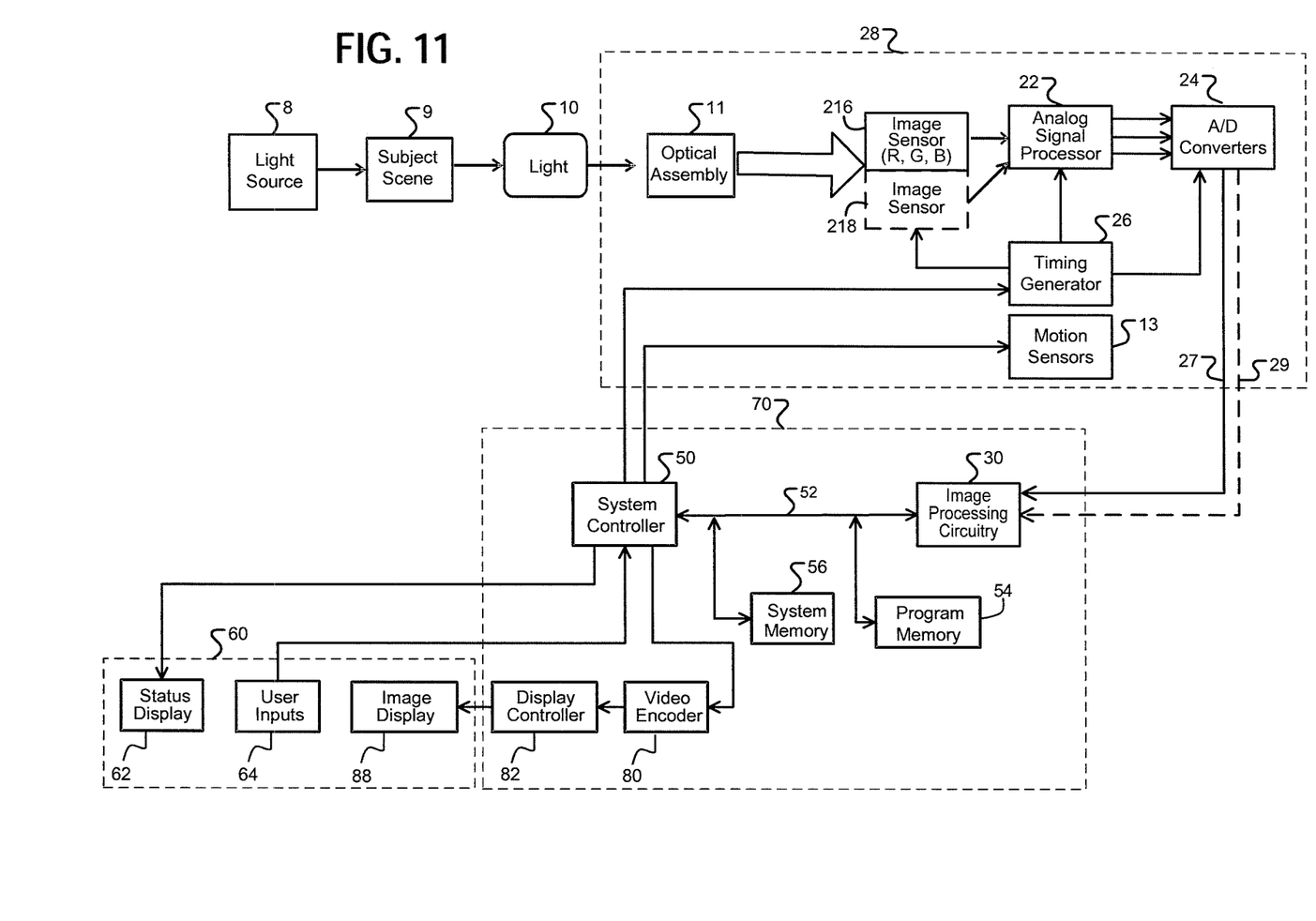
FIG. 11 is a block diagram of an optical instrument system according to an example embodiment of the present invention.

FIG. 11 is a block diagram of an optical instrument system according to an example embodiment of the present invention. While this example circuit is shown for a videoendoscope, the present invention is applicable to more than one type of medical scope instrument, but typically is applicable for scope applications that employ image capture at the instrument distal tip, such as endoscopes, borescopes, or exoscopes, for example, or for other applications in which an image sensor having a steep chief ray angle requirement is desired to be used. In the system of FIG. 11, a light source 8 illuminates subject scene 9 and light 10 reflected from (or, alternatively, as in the case of certain fluorescent or digital microscope arrangements, transmitted or emitted by) the subject scene forms an optical image via an optical channel assembly 11, which includes objective lens group 107 and second lens group 108, where the light is focused, typically aligned with the scope axis or a desired optical axis, passed through any light directing elements (prisms or light splitters), and directed toward the image sensor(s) 216 and optionally 218. If a light splitter is used, light is directed to both sensors as shown by image sensor 218 depicted as a dashed box.

In the present invention, optical channel assembly 11 may be constructed according to the techniques herein and variations thereof. The optical channel assembly 11 may be located in the endoscope distal tip or may be split between the distal tip and the scope shaft and/or camera head, for versions in which a camera head design is employed. Image sensors 216 and 218 convert the incident light to an electrical signal by, for example, integrating charge for each picture element (pixel). The image sensors 216 and 218 may be active-pixel type complementary metal oxide semiconductor sensors (CMOS APS) or charge-coupled devices (CCD), to give just two possible examples. The output analog signal from the image sensors is processed by analog signal processor 22 and applied to analog-to-digital (ND) converter 24 for digitizing the analog sensor signals. In some versions (typically CMOS designs), the analog signal processing and ND converters may be integrated into individual sensor models attached to each sensor 216 and 218.

The image sensors are part of the systems camera 28. The camera 28 generally also includes timing generator 26, which produces various clocking signals to select rows and pixels and synchronizes the operation of image sensors 216 and 218, analog signal processor 22, and ND converter 24. One or more motion sensors 13 such as, for example, an accelerometer, gyro, or magnetometer, may be mounted in the endoscope shaft, tip, or handle to aid in detecting rotation of the endoscope. A scope distal tip electronic assembly typically houses image sensors 216 and 218, while the locations of each of analog signal processor 22, the ND converter 24, and the timing generator 26 may vary, for example in the scope handle 102 or partially integrated into the distal tip electronic assembly. Rigid endoscope designs, or designs using camera heads, may not necessarily place the image sensor(s) and second lens group of the optical channel assembly 11 in the endoscope distal tip. The functional elements of the camera 28 may be fabricated as a single integrated circuit as is commonly done with CMOS image sensors or they may be separately-fabricated integrated circuits.

The system controller 50 controls the overall operation of the image capture device based on a software program stored in program memory 54. This memory can also be used to store user setting selections and other data to be preserved when the camera 28 is turned off. Data connection 27 and data connection 29, which is optional, carry the digital image data of image sensors 216 and 218, respectively, to image processing circuitry 30, which may be integrated with system controller 50 in some versions, or may be a separate programmable logic device or data processor. A data bus 52 provides a pathway for address, data, and control signals. In some variations, data bus 52 may also carry data connections 27 and 29.

Image processing circuitry 30 performs image processing operations including the operations to combine the partial images from image sensors 216 and 218, and to perform rotation functions as further described below. Processed image data are continuously sent to video encoder 80 to produce a video signal. This signal is processed by display controller 82 and presented on image display 88. This display is typically an HD, UHD, or 4K format liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 may manage the graphical user interface (GUI) presented on one or more of the displays (e.g. on image display 88). The GUI typically includes menus for making various option selections.

Image processing circuitry 30, system controller 50, system and program memories 56 and 54, video encoder 80, and display controller 82 may be housed within camera control unit (CCU) 70. The CCU 70 may be responsible for powering and controlling light source 8 and/or camera 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

Image sensors 216 and 218 typically are part of at least one sensing module or assembly that includes a printed circuit board ("PCB") on which is mounted an imaging device including an image sensor with sensing array, typically having a transparent cover. The PCB or other electrical circuitry that reads the sensed signal off the image sensing array of the sensors may be of any suitable type, preferably the smallest and lowest profile available to fit in the limited space. The various portions of the sensor assembly are known and are not shown separately. It will be appreciated by those familiar with imaging sensors that these devices may be accompanied by electronic components such as transistors, capacitors, resistors, and regulators for example.

Those skilled in the art will appreciate that the electronic components and power/data cable may be connected to or included with the image sensor modules in any number of fashions. For example, some embodiments may include the electronic components mounted on the opposite side of PCB on which imaging sensor itself is mounted. The power/data cable may also be connected to the back side of PCB to provide operating power to the image sensors and allow image data to be communicated from the image sensor assembly to processing equipment remote from the shaft distal end portion 106. However, the present invention is not limited to any particular mounting arrangement for electronic components which may accompany imaging sensor and a power/data connection. Any accompanying electronic components and the power/data cable need only be mounted to provide the required function.

Because digital cameras employing endoscopic instruments and related circuitry for signal capture, processing, and correction and for exposure control are well-known, the above description is directed in particular to elements forming part of, or cooperating more directly with, an apparatus in accordance with the present invention. Elements not specifically shown or described herein are selected from those known in the art. Certain aspects of the embodiments may be provided in software. Given the system as shown and described according to the invention in the following materials, software not specifically shown, described or suggested herein that is useful for implementation of the invention is conventional and within the ordinary skill in such arts.

The invention being thus described, it will be obvious that the same may be varied in many ways. Such variations are not to be regarded as a departure from the scope of the invention, and all such modifications as would be obvious to one skilled in the art are intended to be included within the scope of the following claims. For example, reference to an endoscope is intended merely as a representative example application and is not intended to be limiting. Implementations include optical scopes such as exoscopes and borescopes.

Further still, although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can include one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

What is claimed is:

1. An endoscopic instrument, the instrument including:
   (a) an instrument shaft having a distal end portion and a longitudinal axis spanning distal and proximal sides of the distal end portion;
   (b) an image sensor positioned to receive image light through the instrument shaft distal end portion, the image sensor including a sensor array of active areas, and a micro-lens array including a plurality of micro-lenses arranged over the active areas such that the micro-lenses are progressively offset toward an optical center point of the sensor array as a distance from the respective active area to the optical center point increases, the progressive offset varying non-linearly with the distance;
   (c) a lens assembly including (i) an objective lens or lens group positioned in the instrument shaft distal end portion to receive image light from an object space and pass the image light toward the proximal side, and (ii) a second lens group comprising one or more lenses and having negative optical power, the second lens group positioned between the objective lens or lens system and the image sensor, the negative optical power modifying a chief ray angle characteristic of the lens assembly to more closely align with the image sensor and micro-lens array non-linearly progressing offsets.

2. The instrument of claim 1, in which the negative optical power modifies the chief ray angle characteristic of the lens assembly to match a chief ray angle characteristic required by the image sensor and micro-lens array non-linearly progressing offsets.

3. The instrument of claim 2 in which the negative optical power modifies the chief ray angle characteristic of the lens assembly to match the lens assembly to the chief ray angle characteristic required by the image sensor, wherein the chief ray angle characteristic required by the image sensor is at least 20 degrees.

4. The instrument of claim 1, in which the objective lens or lens group, the second lens group, and the image sensor are positioned in the instrument shaft distal end portion.

5. The instrument of claim 1, in which the second lens group includes a plano-concave lens having a planar side facing toward the image sensor, and a plano-convex lens between the plano-concave lens and the image sensor, having a planar side facing the image sensor.

6. The instrument of claim 5, in which the second lens group exhibits a non-linear distortion across at least some of a working area of the second lens group.

7. The instrument of claim 1, in which the second lens group exhibits a non-linear distortion across at least some of a working area of the second lens group.

8. The instrument of claim 1 further comprising a reflecting optical surface between the second lens group and the objective.

9. The instrument of claim 8 wherein the reflecting optical surface comprises a prism.

10. The instrument of claim 8 wherein the reflective optical surface comprises a beam splitter.

11. The instrument of claim 8 wherein the reflecting optical surface and at least some portion of the second lens group having negative optical power are integrated into a single optical element.

12. The instrument of claim 1 wherein the second lens group comprises a plano-convex lens.

13. The instrument of claim 1 wherein the second lens group comprises a surface with negative optical power and a surface with positive optical power.

14. The instrument of claim 1 wherein the second lens group comprises an element with negative optical power and an element with positive optical power.

15. The instrument of claim 14 wherein the objective lens or lens group exhibits a non-linear chief ray angle characteristic.

16. The instrument of claim 1 wherein some part of the second lens group having negative optical power is in contact with the image sensor.

17. The instrument of claim 16 wherein some part of the lens group having negative optical power is cemented to the image sensor.

18. An endoscopic instrument, the instrument including:
   (a) an instrument shaft having a distal end portion and a longitudinal axis spanning distal and proximal sides of the distal end portion;
   (b) an image sensor positioned in the instrument shaft distal end portion, the image sensor including a sensor array of active areas, and a micro-lens array including a plurality of micro-lenses arranged over the active areas such that the micro-lenses are progressively offset toward an optical center point of the sensor array as a distance from the respective active area to the optical center point increases, the progressive offset varying non-linearly with the distance;

(c) a lens assembly including (i) an objective lens or lens group positioned in the instrument shaft distal end portion to receive image light from an object space and pass the image light toward the proximal side, and (ii) a second lens group comprising a plano-concave lens having negative optical power, the plano-concave lens optically arranged adjacent to the image sensor and positioned with a planar side facing the image sensor, the negative optical power modifying a chief ray angle characteristic of the lens assembly to align with the image sensor and micro-lens array progressive offsets.

19. The instrument system of claim 18, in which the image sensor includes a cover glass and the plano-concave lens is bonded to the cover glass.

20. The instrument of claim 18, further comprising a light-directing element between the objective lens group and the second lens group, constructed for re-directing light at 90 degrees toward the second lens group.

21. An endoscopic instrument, the instrument including:
   (a) an instrument shaft having a distal end portion and a longitudinal axis spanning distal and proximal sides of the distal end portion;
   (b) an image sensor positioned in the instrument shaft distal end portion, the image sensor including a sensor array of active areas, and a micro-lens array including a plurality of micro-lenses arranged over the active areas such that the micro-lenses are progressively offset toward an optical center point of the sensor array as a distance from the respective active area to the optical center point increases, the progressive offset varying non-linearly with the distance;
   (c) a lens assembly including (i) an objective lens or lens group positioned in the instrument shaft distal end portion to receive image light from an object space and pass the image light toward the proximal side, and (ii) a second lens group comprising a bi-concave lens having negative optical power, the bi-concave lens optically arranged adjacent to the image sensor, the negative optical power modifying a chief ray angle characteristic of the lens assembly to align with the image sensor and micro-lens array progressive offsets.

22. The instrument of claim 21, in which the image sensor includes a cover glass and the bi-concave lens is bonded to the cover glass.

* * * * *